United States Patent
O'Hara

(10) Patent No.: US 11,621,097 B2
(45) Date of Patent: *Apr. 4, 2023

(54) SYSTEM AND PROCESS FOR PURIFICATION OF ASTATINE-211 FROM TARGET MATERIALS

(71) Applicant: Battelle Memorial Institute, Richland, WA (US)

(72) Inventor: Matthew J. O'Hara, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/586,647

(22) Filed: Jan. 27, 2022

(65) Prior Publication Data

US 2022/0148751 A1 May 12, 2022

Related U.S. Application Data

(63) Continuation of application No. 15/915,283, filed on Mar. 8, 2018, now Pat. No. 11,257,602.

(Continued)

(51) Int. Cl.
*G21G 1/00* (2006.01)
*B01D 15/12* (2006.01)
(Continued)

(52) U.S. Cl.
CPC .............. *G21G 1/001* (2013.01); *B01D 15/12* (2013.01); *B01D 15/14* (2013.01); *B01D 15/20* (2013.01);
(Continued)

(58) Field of Classification Search
CPC .......... G21G 1/001; G21G 2001/0094; B01D 15/12; B01D 15/14; B01D 15/20; B01D 15/426; B01D 59/00; A61K 51/00
See application file for complete search history.

(56) References Cited

U.S. PATENT DOCUMENTS

| 2015/0292061 A1 | 10/2015 | Fassbender et al. |
| 2016/0053345 A1 | 2/2016 | Wilbur et al. |
| 2016/0111176 A1 | 4/2016 | Nolen, Jr. et al. |

FOREIGN PATENT DOCUMENTS

| WO | WO PCT/US2018/021740 | 9/2018 |
| WO | WO PCT/US2018/021740 | 10/2019 |

OTHER PUBLICATIONS

Watanabe, S., et al., "A simple isolation of 211-At using an anion-exchange spin column method," Journal of radioanalytical and nuclear chemistry, 326, pp. 1399-1404. (Year: 2020).*

(Continued)

*Primary Examiner* — Benjamin L Lebron
(74) *Attorney, Agent, or Firm* — Wells St. John P.S.

(57) ABSTRACT

A new column-based purification system and approach are described for rapid separation and purification of the alpha-emitting therapeutic radioisotope $^{211}$At from dissolved cyclotron targets that provide highly reproducible product results with excellent $^{211}$At species distributions and high antibody labeling yields compared with prior art manual extraction results of the prior art that can be expected to enable enhanced production of purified $^{211}$At isotope products suitable for therapeutic medical applications such as treatment of cancer in human patients.

8 Claims, 3 Drawing Sheets

Related U.S. Application Data

(60) Provisional application No. 62/487,290, filed on Apr. 19, 2017.

(51) Int. Cl.
   | | |
   |---|---|
   | *B01D 15/14* | (2006.01) |
   | *B01D 15/42* | (2006.01) |
   | *B01D 15/20* | (2006.01) |
   | *B01D 59/20* | (2006.01) |
   | *A61K 51/00* | (2006.01) |

(52) U.S. Cl.
   CPC .......... *B01D 15/426* (2013.01); *B01D 59/20* (2013.01); *A61K 51/00* (2013.01); *G21G 2001/0094* (2013.01)

(56) References Cited

OTHER PUBLICATIONS

Li, Y., et al., "Investigation of a tellurium-packed column for isolation of astatine-211 from irradiated bismuth targets and demonstratio of a semi-automated system", Scientific Reports, 91: 16960 (Year: 2019).*

Anaheim, E., et al., "Automated astatination of biomolecules—a stepping stone towards multicenter clinical trials", Scientific Reports, 5:12025, DOI: 10 1038/srep12025, 2015, 1-11.

Balkin, E.R., et al., Evaluation of a Wet Chemestry Method for Isolation of Cyclotron Produced [211At] Astatine, Applied Sciences, 3, 2013, 636-655.

Haas, R.A., Amberchrom CG71 Chromatographic Grade Resin for Chromatographic Purification, 2007, http://www.dow/assets/attachments/business/process_chemicals/amberchrom_cg17m/tds/amerrchrom_cg71.pdf.

Office Action for U.S. Appl. No. 14/832,554, dated Jan. 9, 2018.

O'Hara, M.J., et al., An automated flow system inconporating in-line acid dissolution of bismuth metal from a cyclotron irradiated target assembly for use in the isolation of astatine-211. Applied Radiation and Isotopes, 22, 2017, 202-210.

Thomas Scientific, "Mini Spe-ed Cartridges", Thomas Scientific Dec. 21 (Year: 2020).

Wilbur, et al., "Evaluation of Novel Wet Chemistry Separation and Purification Methods to Facilitate Automation of Astatine-211 Isolation", Final Report DE-SC0010502, U.S. Department of Energy, Jul. 19, 2016, United States, 52 pages.

* cited by examiner

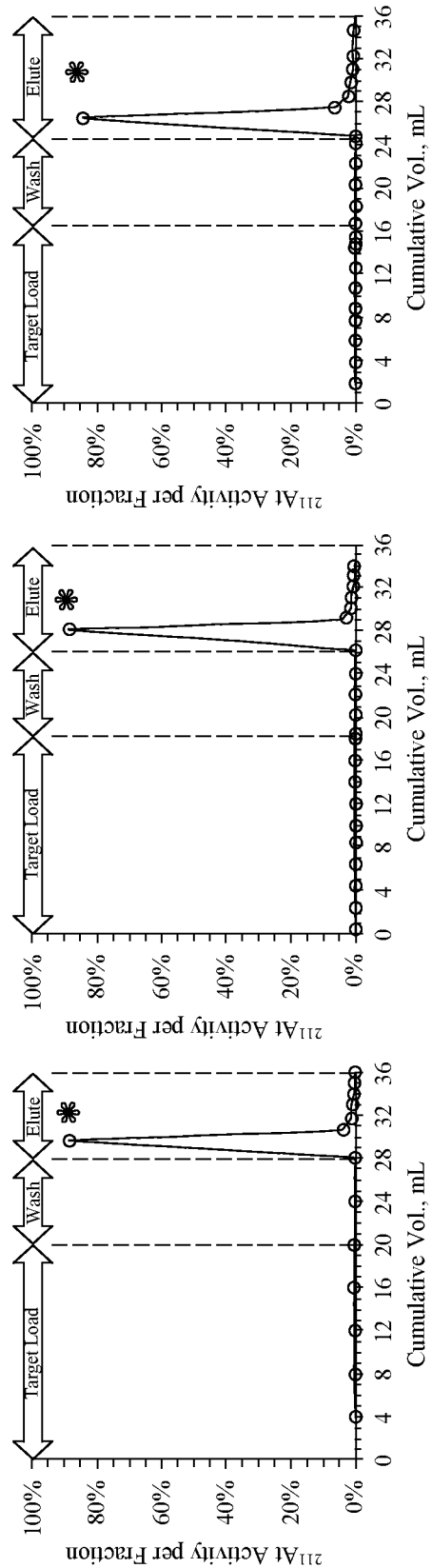

SYSTEM AND PROCESS FOR PURIFICATION OF ASTATINE-211 FROM TARGET MATERIALS

CLAIM TO PRIORITY

This application is a continuation of U.S. patent application Ser. No. 15/915,283 filed Mar. 8, 2018, which claims priority to and the benefit of U.S. Provisional Patent Application Ser. No. 62/487,290 filed Apr. 19, 2017, the entirety of each of which is hereby incorporated by reference.

STATEMENT REGARDING RIGHTS TO INVENTION MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

FIELD OF THE INVENTION

The present invention relates generally to radionuclide separation systems and processes and more particularly to a system and process for enhanced purification of Astatine 211 ($^{211}$At) from target materials for use in medical applications.

BACKGROUND OF THE INVENTION $^{211}$At is a promising therapeutic isotope for use in medical applications including treatment of cancers in humans such as lymphoma and leukemia. While still in the clinical trials stage, the demand for this isotope can be expected to rise dramatically. Presently, there are no commercially available fully automated systems and approaches available to provide this valuable radioisotope in a highly purified and standardized form for use in these various medical applications. While existing methods such as liquid/liquid extraction approaches exist, this manual approach that is labor intensive, dose-intensive and time consuming. These factors coupled to the fact that $^{211}$At also has a half-life of only ~7 h renders such an arrangement of limited application.

Another approach known in the art for preparation of the $^{211}$At isotope is a furnace distillation process that volatilizes $^{211}$At from an irradiated bismuth (Bi) target obtained from a cyclotron. However, high temperatures needed to volatilize the $^{211}$At from the target often results in some volatilization of Bi from the target which contaminates the recovered 211At resulting in an unpurified product. This approach has also been shown to work best on low-mass Bi targets raising concerns that these low-mass Bi targets may not be suitable for scaling needed to generate hundreds of mCi of $^{211}$At for near-term clinical trials and beyond. Additionally, production of a gaseous $^{211}$At product raises other radiological protection concerns given the potential for catastrophic release of the gaseous radionuclide into either the work space or release from a stack should the furnace assembly rupture during $^{211}$At distillation.

While various attempts have been made in arriving at a column based or even automated process for obtaining $^{211}$At, the PEG column method as proposed by Wilbur et. al in US Patent Pub No. 2016/0053345 simply has not demonstrated efficacy or operability. See A. L. Wooten, M.-K. Chyan, et al., "PEG column studies designed to eliminate nitric acid distillation in automation of the wet chemistry approach to isolation of astatine-211", 16th International Workshop on Targetry and Target Chemistry, Santa Fe, N. Mex., AIP Conference Proceedings (2016). "While that result was encouraging, only ~13% of the captured $^{211}$At was removed from the PEG column with the use of concentrated NH$_4$OH as the eluent. Given these drawbacks in the prior art, a continuing need exists for new and effective $^{211}$At purification process." The present invention is a significant advance in this direction.

Additional advantages and novel features of the present disclosure will be set forth as follows and will be readily apparent from the descriptions and demonstrations set forth herein. Accordingly, the following descriptions of the present disclosure should be seen as illustrative of the disclosure and not as limiting in any way.

SUMMARY

The present disclosure provides examples of systems and methods for the separation of $^{211}$At from dissolved cyclotron targets using small columns with preselected flow rates to achieve the separation in minutes. As will be described hereafter, these embodiments provide (1) lower processing complexity compared to the prior art with fewer and simpler process steps; (2) reduced preparation time for purified $^{211}$At product fractions for clinical uses and applications compared to the prior art extraction approach; (3) automated capabilities allowing remote handling and processing in shielded environments thus reducing radiation doses to personnel stemming from handling and contact; (4) purified product fractions in a low elution volume enabling rapid removal of the liquid volume for transport of the purified $^{211}$At product, for example, as a salt; (5) a $^{211}$At product of superior purity and consistent quality; (6) a purified $^{211}$At product with a superior distribution of a preferred species of isotope; and (7) a purified product with a comparable or better antibody labeling efficiency that can be expected to be advantageous for medical and therapeutic applications.

In one example, a dissolved sample containing $^{211}$At is loaded on to a column wherein the desired $^{211}$At materials are then captured. The column is then washed and the resulting $^{211}$At materials are then eluted from the column using specified materials and conditions. Specifically in one example, a method for producing a purified $^{211}$At isotope product is described wherein a dissolved cyclotron target solution containing $^{211}$At isotopes is passed through a separation device including a column with preselected packing material to recover $^{211}$At isotopes from the dissolved target solution included within. In some instances the captured $^{211}$At isotope is later eluted from the preselected packing material and captured in a collection device. In some instances, the dissolved target solution includes Bi nitrate salts and $^{211}$At dissolved in an acid such as hydrochloric acid (HCl) solution. A conditioning solution and/or a wash solution can also be utilized before or after the loading on the column to enhance the capture and/or recovery of materials from the column. In one example, the pre-selected packing material within the column is a macroporous polymer resin.

This can all be performed using a fluidic system that includes a target solution containing bismuth salts and $^{211}$At isotopes dissolved in an acid and tubing operatively connected to separation column through a valve so as to enable delivery of the target solution to the separation column at a preselected flow rate. In use the target solution is passed through the separation column and $^{211}$At isotopes are collected on a packing material within the separation column.

In one particular set of examples a clinically useful single dose amount of $^{211}$At was obtained using only 20 mL to load the target on the column, 8 mL to wash the column, and then eluted in ~2 mL while retaining 88% of activity as compared to ~78% average for other method such as the method set forth in the article "Evaluation of a Wet Chemistry Method for Isolation of Cyclotron Produced [$^{211}$At] Astatine" by Balkin et. al., *Appl. Sci.* 2013, 3(3), 636-655; doi:10.3390/app3030636 referred to at times as the Wilbur method, after the corresponding author on the paper.

Isolated $^{211}$At samples obtained from the method described in the present application used 'next day' had >70% labeling efficiency using a CA10-B10 antibody, thus supporting the desired aim of a process capable of producing a pure product at a high yield with a consistent quality and purity, and suitable labeling properties. Such a process can be automated to minimize need for sample contact by personnel with the associated radiation doses and enable reduced processing time. This process eliminates a need for complicated and multi-step manual processing steps; minimizes waste products; and addresses other drawbacks and limitations imposed by manual processing systems.

The purpose of the foregoing abstract is to enable the United States Patent and Trademark Office and the public generally, especially the scientists, engineers, and practitioners in the art who are not familiar with patent or legal terms or phraseology, to quickly determine the nature and essence of the technical disclosure of the application. The abstract is neither intended to define the invention of the application which is measured by the claims nor is it intended to be limiting as to the scope of the invention in any way.

BRIEF DESCRIPTION OF THE DRAWINGS

FIGS. 3(a)-3(c) show column effluent activity fractions for $^{211}$At during target load/wash/$^{211}$At elute steps, presented as the $^{211}$At isolation process performed across three cyclotron bombarded and dissolved Bi targets.

DETAILED DESCRIPTION

The present disclosure provides examples and descriptions of enhanced purification and chemical isolation of $^{211}$At for medical and therapeutic applications such as diagnosis and treatment of cancer in patients. In many of these examples purification using a separation column with a small internal volume as low as ~0.25 cc provides substantially quantitative extraction of $^{211}$At from dissolved cyclotron targets at selected flow rates. These separation columns can be packed, for example, with an uncoated material containing a macroporous polymeric resin such as AMBERCHROM® CG-71s that is sandwiched in the column, for example, between two acid-resistant frits.

Figure 1:
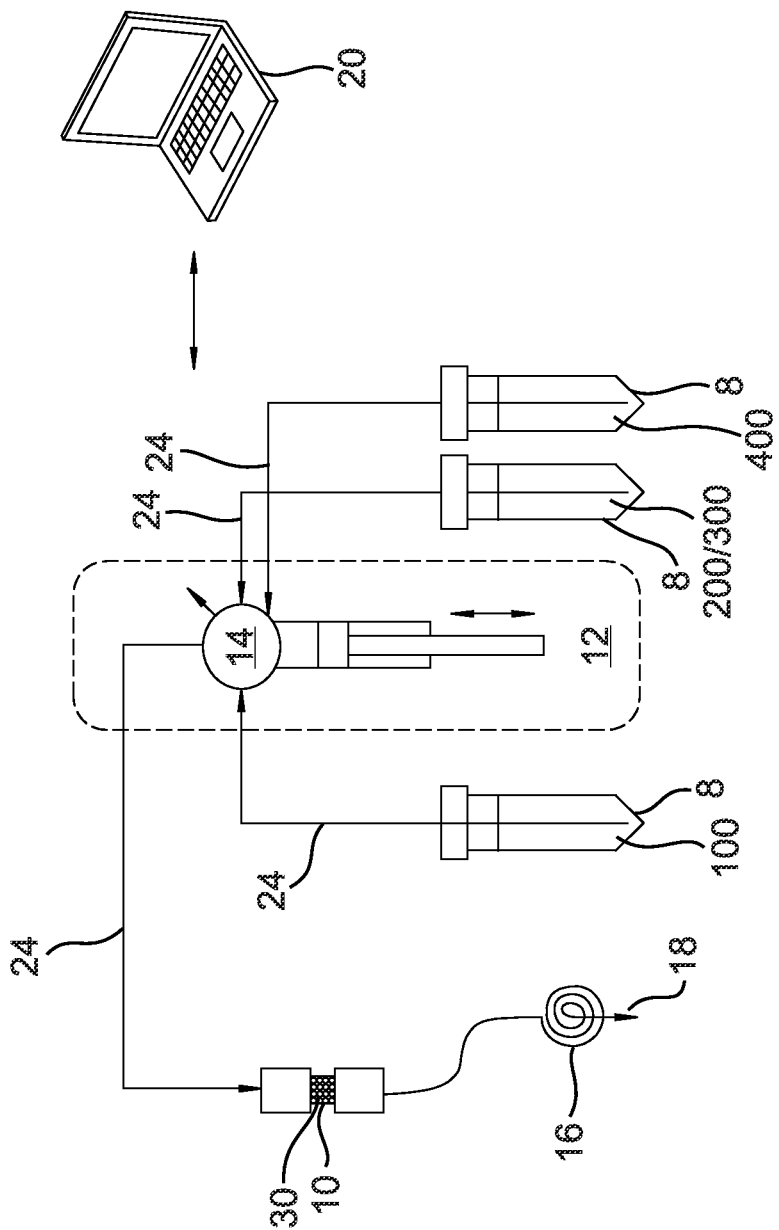
FIG. 1 shows one embodiment of a system of the present invention for automated isolation of an $^{211}$At isotope product.

Various examples and embodiments of specific disclosures are provided hereafter and described in the attached drawings. Referring first to FIG. 1, a separation system and approach for production of a purified radioisotope $^{211}$At product from dissolved cyclotron targets for therapeutic applications is shown and described. Referring first to FIG. 1, in this system, a vessel 8 containing a dissolved bismuth target solution 100, for example, in an acid that contains the desired $^{211}$At isotope to be obtained is connected by tubing 24 to a fluid distribution valve 14 such as a multiple flow path distribution valve which is also connected by tubing to various other features of the device such as the separation column 10, as well as vessels 8 that contain solutions (100, 200, 300, 400). A syringe pump 12 coupled to distribution valve 14 is configured to deliver solutions (100, 200, 300, 400) at selected flow rates to a separation column 10 filled with a selected packing material 30. From this column 10 solutions are passed by tubing past a detector 16 and on to a fraction collector 18. In other embodiments such as the configuration of FIG. 2, multiple pumps (12, 12') and valves (14, 14') can be included. In addition a gate valve 26 that separates product from waste can be included instead of or in addition to the detector 16 and collector 18 shown in FIG. 1. The entire operation can be controlled by a computer 20.

Figure 2:
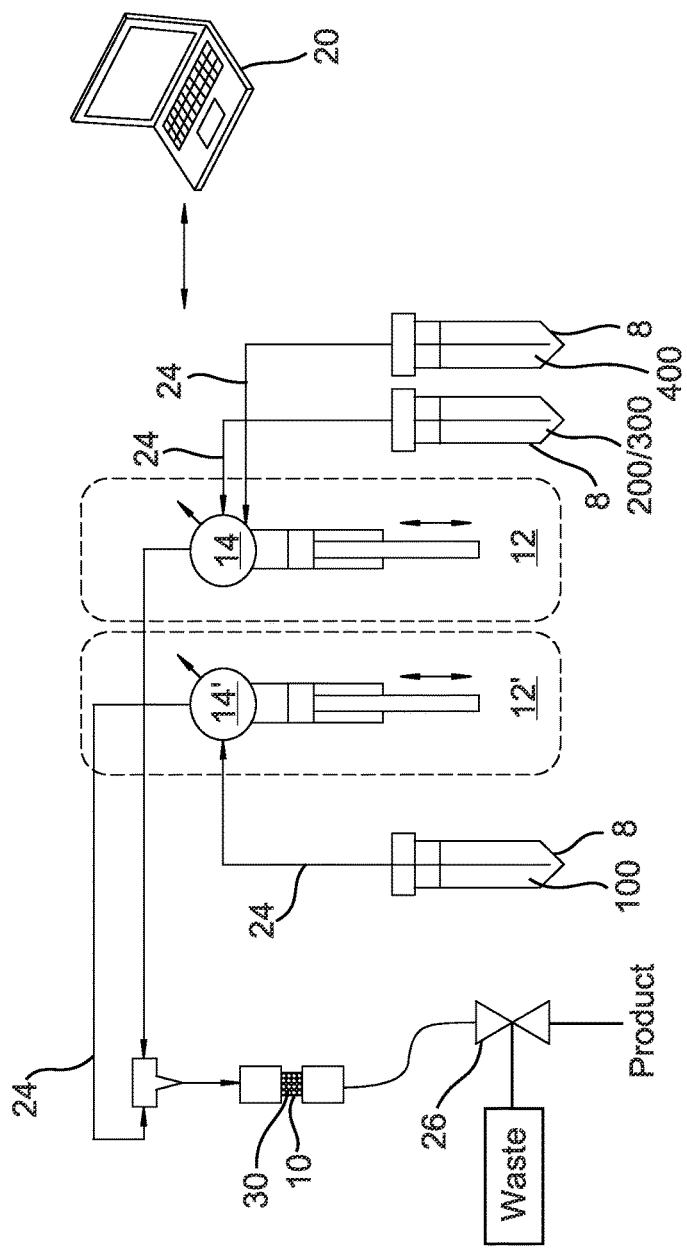
FIG. 2 shows a second embodiment of a system of the present invention for the automated isolation of an $^{211}$At isotope product.

In this approach, the bismuth target is dissolved in nitric acid of a selected molar concentration to form a target solution 100 containing dissolved bismuth ions and dissolved $^{211}$At isotope ions. In another step nitric acid in the solution containing the dissolved Bi isotope ions and $^{211}$At isotope ions is subsequently removed, for example, by distilling the dissolved target solution that forms stable nitrate salts of both the Bi and $^{211}$At isotopes. Next, these Bi and $^{211}$At nitrate salts are redissolved in hydrochloric (HCl) acid solution at a selected molar concentration and introduced to the containment vessel 8 filled with prepared dissolved target solution 100 for column separation. The target solution 100 is then passed through the separation column 10 packed with a selected packing material such as, e.g., macroporous CG-71 polymer resin or another suitable material at a preselected flow rate to separate the $^{211}$At isotope ions from the dissolved bismuth target solution. Separated $^{211}$At isotope ions are retained on the packing material in the separation column 10 and the $^{211}$At depleted bismuth target solution passes from the column for subsequent collection as shown in FIG. 1 or waste as shown in FIG. 2.

In one instance, the process operates by conditioning the system by passing an acidic conditioning solution 200 through the system to establish the desired acidity and loading conditions and enhance the loading of the $^{211}$At ions in the target solution on to the column. Next, a target solution 100 containing $^{211}$At dissolved in a Bi target is added to the system and loaded on to the columns 10. (In some instances a small volume of air can be dispensed into the column influent line to remove the remaining conditioning fluid present in the system prior to loading.) Once loaded on to the columns the materials can be allowed to rest for a period of time and then washed using an acidic wash solution 300. (In some instances the conditioning solution and the wash solution are the same) The $^{211}$At is then eluted from the column using a eluent solution 400 from whence the target material can be processed for clinical delivery.

In one example system and process were used in an example wherein conditioning took place by passing 5 mL of 8M HCl at a flow rate less than or equal to 2 ml/min, followed by passing a small volume of air through the lines. After passing the air through the lines, 15-20 mL of a target solution containing $^{211}$At dissolved in a Bi target was added to the system at a low rate less than or equal to 2 mL/min loaded on to the columns.

In this instance the target solution contained a Bi mass between 3.5 and 6 g which had been dissolved using $HNO_3$, in this process the $HNO_3$ was then distilled away and the remaining salts re dissolved in 8M HCl. This bismuth target dissolution can be performed by an automated process such as the one described by O'Hara et al in article entitled "An automated flow system incorporating in-line acid dissolution of bismuth metal from a cyclotron irradiated target assembly for use in the isolation of astatine-211", Applied Radiation and Isotopes 122 (2017) 202-210. The contents of which are herein incorporated by reference. This system for a distillation assembly and a process for dissolving the resulting bismuth nitrate salt to form the target solution are described therein. Such a system can also be functionally interconnected with the systems such as those shown in FIG. 1 or 2 to form a complete automated system for separations. While these methods and systems are described for forming the target solution it is to be distinctly understood that the implementation is not limited thereto but may be variously alternatively embodied, according to the needs and necessities of a user.

After the loading sequence 8 mL of 8M HCl was then used as a wash solution and passed through the system at a flow rate of less than or equal to 2 mL/min. An eluent solution consisting of 8 mL of 10M $HNO_3$ was then passed through the system at flow rate of 1 mL/min to elute the isolated $^{211}$At from the column. A resulting 211At product fraction, examples of which are shown in FIGS. 3(a)-3(c) were isolated in about 1.5 mL.

Testing of the eluted $^{211}$At demonstrated that while chemical yields were high, preferably greater than or equal to about 70%, more particularly greater than or equal to about 90%, and yet more particularly greater than or equal to about 95%. The present invention also recovers $^{211}$At ions from the column at recovery yields greater than or equal to about 95%. The present invention also reduces process complexity enabling significantly shorter processing times as low as 20 minutes or better compared with the generally longer processing times (up to 3× greater) of the prior art solvent extraction process. Automated processing provided by the present invention also reduces radiation doses to personnel stemming from sample contact and handling that is not addressed in the manual solvent extraction process described above.

In other alternative embodiments and configurations such as the example, shown in FIG. 2 a pair of syringe pumps and distribution valves are used with one pump and valve utilized, for example, for column conditioning, washing, and eluting with the other pump and valve utilized, for example, for handling the dissolved target. Packing material in the separation column recovers and retains the $^{211}$At isotope from the dissolved target solution on the column packing material until the $^{211}$At isotope is eluted from the column. In the preferred embodiment, packing material utilized for separation, recovery, and purification of the $^{211}$At isotope from the dissolved bismuth target is a macroporous polymeric resin such as AMBERCHROM CG-71s or another suitable packing material. An optional detector, such as a radiochromatography detector capable of monitoring $^{211}$At activity in column effluents, can be coupled to the separation column.

In some embodiments the radiochromatography detector is a NaI(TI) scintillation detector. Other detectors may also be utilized. An optional fraction collector is shown coupled to the detector for collection of column effluents. In this embodiment the system also includes a control computer for automated control of system components as well as separation process parameters such as, for example, distribution valve flow channel and syringe pump delivery volumes as well as dissolved target and eluent flow rates. Control of other system components and processing parameters are also envisioned.

As described above exemplary tests utilized a flow rate≤2.0 mL/min but faster or slower flow rates may be utilized and are thus not intended to be limited. The separation column can also be pre-conditioned in a preparatory step with a small volume(s) of hydrochloric acid (HCl). In addition, clean HCl solution can be introduced to the column to wash any residual traces of target solution from the column yielding a highly purified $^{211}$At product prior to the elution step. $^{211}$At product elution profiles are controlled in part utilizing higher or lower $HNO_3$ concentrations and are thus not intended to be limited. In one example, 10 M $HNO_3$ was utilized to efficiently remove sorbed $^{211}$At isotope ions from the column. Eluted $^{211}$At product solutions can then be neutralized with a small quantity of strong base (NaOH) to create a solution having a desired pH, preferably a nearly neutral or neutral solution.

In one set of tests, one embodiment of the automated fluidic system described above was utilized and operated to process a full-scale Bi target containing ~14 mCi $^{211}$At. The column utilized a resin bed of dimensions ~5.7 mm dia.×~11.3 mm tall. Packing material in the separation column was a macroporous, polymeric resin (e.g., AMBERCHROM CG-71 ROHM and HAAS utilized conventionally to separate biomolecules including proteins, peptides, and nucleic acids) of a generally small particle size, preferably at or below about 120 microns (μm), more preferably at or below about 75 μm, and most preferably at or below about 35 μm. Other packing materials are also envisioned. The packing material for separation and purification of the $^{211}$At isotope was positioned within the column sandwiched between two acid-resistant frits such as glass fiber frits or polymer (e.g., polyethylene) frits. $^{211}$At activity in all column effluents was monitored utilizing a NaI(TI) scintillation radiochromatography detector. Column effluents were collected as fractions of known volume in a fraction collector. Table 1 shows the information related to various Bi target masses and the activity of the $^{211}$At in each of the outlined cyclotron bombarded targets.

TABLE 1

| Run Date | Bi Target Mass, g | $^{211}$At Activity, mCi (EOB) |
|---|---|---|
| Dec. 8, 2016 | 4.54 | 13.2 |
| Feb. 1, 2017 | 5.54 | 26.8 |
| Apr. 5, 2017 | 3.29 | 24.0 |

In another set of experiments a Bi target irradiated in a cyclotron containing ~25-30 mCi $^{211}$At was dissolved in 10 M $HNO_3$ for a total volume of 15.5 mL. 50% (7.75 mL) of the solution was removed as a duplicate sample and replaced with 7.75 mL of 2.2 g non-irradiated Bi metal separately dissolved in 10 M $HNO_3$ so as to provide ~100% of the original Bi and original volume of $HNO_3$ found in the originally dissolved target. $HNO_3$ was distilled from the solution in a distillation chamber leaving a salt cake of Bi nitrate salts. These salts were redissolved in 8 M HCl to yield a final solution volume of 18.75 mL (0.242 g Bi/mL). The sample container containing the final solution (4.54 g dissolved Bi and ~13.2 mCi $^{211}$At) was connected to the fluid delivery system and processed. A second cyclotron target sample with 5.54 g Bi metal containing ~27 mCi $^{211}$At was also dissolved and processed. A third sample containing 3.29 g Bi metal containing about 24 mCi $^{211}$At was also dissolved and processed.

FIGS. 3A-3C show column separation profiles for $^{211}$At products resulting from replicate purification runs obtained from separate cyclotron irradiated Bi targets. Asterisks (*) in these figures represent volumes of the $^{211}$At product fractions of between 1.5 and 2.0 mL selected for subsequent species distribution and antibody labelling tests. These volumes are not intended to be limiting.

Column effluent volumes are shown (FIGS. 3A-3C) during which the dissolved target loading, column washing, and column eluting steps were performed. During column elution, $^{211}$At elution profiles were traced with the radiochromatography detector so that the fraction collector could collect the purified $^{211}$At isotopes in a minimum volume. Single peaks in these figures correspond to $^{211}$At product fractions recovered for subsequent speciation distribution and antibody labeling tests. Volumes of individual $^{211}$At fractions were analyzed by dose calibrator. Percent activity for each fraction was calculated by taking each fraction volume and dividing by the total activity recovered in the process (column effluent fractions+activity remaining on the column+activity remaining in the vessel that originally contained the dissolved target+activity in waste vessels). Table 2 lists results for the purification approach and $^{211}$At activity results obtained in each step of the purification process for the 13 mCi, 27 mCi, and 24 mCi $^{211}$At target samples, respectively.

TABLE 2

| | Dec. 8, 2016 Column Effluent Recoveries | | Feb. 1, 2017 Column Effluent Recoveries | | Apr. 5, 2017 Column Effluent Recoveries | |
|---|---|---|---|---|---|---|
| Step | Activity, mCi | Activity Distribution, % | Activity, mCi | Activity Distribution, % | Activity, mCi | Activity Distribution, % |
| Col. Condition | — | — | — | — | — | — |
| Dissolved Target Load | 0.144 | 1.1 | 0.062 | 0.2 | 0.040 | 0.2 |
| Col. Wash | 0.0283 | 0.2 | 0.011 | 0.0 | 0.010 | 0.0 |
| Elute | 12.601 | 95.5 [b] | 25.7 | 96.1 [c] | 22.950 | 95.6 [d] |
| Residue on Column | 0.420 | 3.2 | 0.622 | 2.3 | 0.564 | 2.3 |
| Misc. waste streams | | | 0.728 | 2.7 | 0.439 | 1.8 |
| Target Total | 13.2 | 100 | 26.8 | 102 | 24.0 | 101 |

[a] Activities reported for end-of-bombardment (EOB)
[b] Activity in all elute fractions; the isolated $^{211}$At fraction used for antibody labeling contained 88.4% of the target activity in 1.56 mL
[c] Activity in all elute fractions; the isolated $^{211}$At fraction used for antibody labeling contained 88.5% of the target activity in 1.96 mL
[d] Activity in all elute fractions; the isolated $^{211}$At fraction used for antibody labeling contained 84.4% of the target activity in 1.64 mL Results in Table 2 show that of the total 13.2 mCi, 27 mCi, and 24 mCi $^{211}$At obtained from the three targets and loaded onto the columns (at end-of-bombardment, EOB), ~96% of the total activity was collected during column elution. Isolated product fractions were also collected in a small volume (1.56 mL, 1.96 mL, and 1.64 mL) with two containing ~88% and one containing about 84% of the total $^{211}$At activity. Only ≤1.1% activity was lost to the column during the loading and washing steps. And only ~2-3% activity remained in the column resin bed or frits after $^{211}$At elution. In this exemplary approach, the column-based method invention yields highly purified $^{211}$At that is released in a low volume acidic product fraction (e.g., 10 M $HNO_3$). By comparison, the prior art manual extraction method as set out in the Balking publication has a general yield distribution of 78±11%.

Two characteristic astatine peaks appear in the HPLC chromatograms from HPLC assays which are labeled as peak 1 and peak 2. Astatine Peak 1 behaves like iodate and is thus referred to as "astatate". Astatine Peak 2 behaves like iodide and is thus referred to as "astatide". Maximum tolerance for Peak 1 in the prior art approach is 15%. Peak 2 is a preferred species for establishing antibody labeling efficacy. Minimum threshold quantity of this species obtained in any purified $^{211}$At product fraction in the prior art approach generally must be greater than or equal to 85%. Table 3 shows that purified $^{211}$At product fractions of the present invention are substantially comprised of the preferred efficacious "astatide" species easily surpassing threshold quality metrics established for the prior art L/L extraction approach.

TABLE 3

| | | Peak 1 ("astatate"), % | Peak 2 ("astatide"), % |
|---|---|---|---|
| | | UW $^{211}$At Product Criteria | |
| Processing Date | | ≤15 | ≥85 |
| Dec. 8, 2016 | Column Product (pH ~13) | 6 | 94 |
| Feb. 1, 2017 | Column Product (pH ~13) | 8 | 92 |
| | Column Product (pH ~6.5, after acid swing) | 2 | 98 |
| | Column Product (after taken to salts and brought to pH ~6.5) [a] | 0.1 | 99.9 |
| Apr. 5, 2017 | Column Product (pH ~14) | 4.5 | 95.5 |
| | Column Product (after taken to salts and brought to pH ~6.5) (solution reconstituted in 50% the original vol.) [a] | 12.7 | 87.3 |

[a] $^{211}$At solution reconstituted in phosphate buffered saline; has twice the dissolved solids concentration as it had originally In another set of tests, labeling efficiency of purified $^{211}$At isotopes obtained by the present invention to boron-10 (B-10) conjugated CA10 antibodies was determined. $^{211}$At nitrate salts generated by the present invention were dissolved in a phosphate buffered saline (PBS) solution. 211At labeling measurements onto the B-10 conjugated CA10 antibodies were collected for each of the two separate column-generated $^{211}$At product fractions in duplicate using two 0.5 mL aliquots or 1.0 mL aliquots of phosphate buffered saline (PBS)-dissolved $^{211}$At solution. Table 4 lists antibody labeling results for each of the 13.2 mCi, 27 mCi, and 24 mCi $^{211}$At column-generated samples performed in at least duplicate.

TABLE 4

| Processing Date | Sample | Product Vol. Labeled, mL | Mass of Antibody, Mg | Labeling Yield, % |
|---|---|---|---|---|
| Dec. 8, 2016 | A [a] | 0.5 | 0.5 | 76.3 |
| | B [a] | 0.5 | 0.5 | 73.4 |
| Feb. 1, 2017 | A [b] | 1.0 | 1.0 | 83.8 |
| | B [c] | 1.0 | 1.0 | 80.7 |

TABLE 4-continued

| Processing Date | Sample | Product Vol. Labeled, mL | Mass of Antibody, Mg | Labeling Yield, % |
|---|---|---|---|---|
| Apr. 5, 2017 | A [b] | 0.5 | 1.0 | 82.6 |
| | B [b] | 0.5 | 0.2 | 79.5 |
| | C [c] | 0.5 | 1.0 | 77.3 |

[a] Replicate labeling experiments occurred the next day; performed on post-neutralized $^{211}$At product
[b] Post-neutralization of $^{211}$At product
[c] Post-neutralization, evaporation to dryness, and reconstituted in phosphate buffered saline Slightly lower labeling yields were obtained for the 13 mCi samples as they were performed a day following $^{211}$At isolation. Yet, results were still comparable to fresh $^{211}$At product results obtained utilizing the prior art manual extraction method. Results demonstrate that purified $^{211}$At products of the present invention exhibit comparable to better labeling efficiencies compared to the prior manual extraction method. In addition to the sample examples provided in additional embodiments the use of a PD-10 size exclusion column served as an effective means to remove nitrate salts from the labeling fluid during the step wherein protein is separated prior to patient injection. FIG. 3 shows column effluent activity fractions for $^{211}$At during target load/wash/$^{211}$At elute steps. Asterisks indicate single $^{211}$At product fraction that was isolated for $^{211}$At speciation monitoring by HPLC, $^{211}$At antibody labeling, and Bi metal contamination. Table 5 shows results from PD-10 size exclusion separation of $^{211}$At labeled CA10-B10 antibody from labeling solvent for labeling experiments A and C from the final Apr. 5, 2017 run which contained about 24 mCi of $^{211}$At. Table 6 shows the Residual Bi contamination in column-generated $^{211}$At product fractions as determined by inductively coupled plasma—mass spectrometry analysis of $^{211}$At product fraction. The February 1 run was not as good as the April 5 run. This is because the February 1 run used the single pump set-up from FIG. 1 and the April 5 run used the dual pump set-up from FIG. 2.

TABLE 5

| Antibody-bearing Fraction | $^{211}$At Activity, µCi [a] | Nitrate conc., µg/mL [b] |
|---|---|---|
| A5 | 181 | <0.2 |
| A6 | 850 | <0.2 |
| A7 | 1077 | <0.2 |
| A8 | 561 | <0.2 |
| A9 | 78 | <0.2 |
| A10 | 18 | <0.2 |
| C5 | 313 | <0.2 |
| C6 | 995 | <0.2 |
| C7 | 1088 | <0.2 |
| C8 | 369 | <0.2 |
| C9 | 40 | <0.2 |
| C10 | 12 | <0.2 |

[a] At end of beam (EOB)
[b] Values are below the reported limit of quantification (LOQ) of the instrument

TABLE 6

| Processing Date | $^{211}$At Product Fraction Vol, mL [b] | Bi contamination, µg/mL | Total Bi in Product Fraction, µg | Bi Decontamination Factor [e] |
|---|---|---|---|---|
| Feb. 1, 2017 | 1.96 | 42.1 [c] | 65.7 | 8.43 × 10⁴ |
| Apr. 5, 2017 | 1.64 | 9.6 [d] | 15.7 | 2.10 × 10⁵ |

[a] As determined by ICP-MS analysis of $^{211}$At product fraction
[b] From Table 4
[c] Results obtained on process that utilized only a single syringe pump to deliver dissolved Bi target and perform column condition/wash/elute steps (FIG. 1)
[d] Results obtained on a process that utilized a separate syringe pump to deliver dissolved Bi target, and one to perform column condition/wash/elute steps (FIG. 2)
[e] Based on ratio of initial Bi mass in bombarded target (see Table 3) to the Bi mass in the $^{211}$At product fraction (column 4, this table)

This data shows that despite the fact that the $^{211}$At/antibody labeling solution contained multi-molar nitrate concentration (originally from the 10M HNO3 $^{211}$At column eluent that required neutralization with NaOH (thereby creating a solution of 10M NaNO3), the size exclusion separation process prevented the high nitrate levels from passing through the PD-10 column and into the final isolated $^{211}$At-labeled protein fractions.

In some embodiments, purified $^{211}$At isotopes in the nearly neutral or neutral product solutions are directly labeled with the selected antibody. In some embodiments, liquid from the solution is removed, for example, in a centrifugal evaporator system to create a $^{211}$At product salt (e.g., nitrate salt) that stabilizes the $^{211}$At isotopes for transport for end use in clinical and medical applications. In another embodiment, nitrate in the solution can first be decomposed to form an alternate salt such as a chloride salt or a hydroxide salt for transport.

The present application makes clear that the system and method of the present invention provides several advantages over the prior art. The present invention (1) has a lower processing complexity compared to the prior art with fewer and simpler process steps; (2) reduces preparation time for purified $^{211}$At product fractions for clinical uses and applications compared to the prior art extraction approach; (3) is automated allowing remote handling and processing in shielded environments thus reducing radiation doses to personnel stemming from handling and contact; (4) provides purified product fractions in a low elution volume enabling rapid removal of the liquid volume for transport of the purified $^{211}$At product, for example, as a salt; (5) provides a $^{211}$At product of superior purity and consistent quality; (6) provides a purified $^{211}$At product with a superior distribution of a preferred species of isotope; and (7) provides a purified product with a comparable or better antibody labeling efficiency that can be expected to be advantageous for medical and therapeutic applications.

While a number of embodiments of the present invention have been shown and described, it will be apparent to those skilled in the art that many changes and modifications may be made without departing from the invention in its broader aspects. The appended claims are therefore intended to cover all such changes and modifications that fall within the scope of the invention.

What is claimed is:

1. A method for producing a purified $^{211}$At isotope product from dissolved cyclotron targets, the method comprising:
   providing a separation media associated with $^{211}$At isotopes; and passing an At elution solution comprising $HNO_3$ through the separation media to elute $^{211}At$ isotopes from the separation media and provide $^{211}At$ isotopes in an $HNO_3$ solution.

2. The method of claim 1 wherein the providing the separation media associated with $^{211}At$ isotopes comprises:
preparing the separation media with conditioning solution comprising HCl to acidify the separation media; and
passing a $^{211}At$/Bi solution through the separation media to associate $^{211}At$ isotopes with the media and recover Bi as an eluent.

3. The method of claim 2 further comprises dissolving a composition of $^{211}At$ and Bi-nitrate salts in an HCl solution to form the $^{211}At$/Bi solution comprising the $^{211}At$ and Bi in an HCl solution.

4. The method of claim 3 further comprising dissolving a cyclotron target containing $^{211}At$ and Bi in a nitric acid solution to form the composition comprising $^{211}At$ and Bi-nitrate salts.

5. The method of claim 1 wherein the At elution solution has a molarity between 7.5M and 15.8M.

6. The method of claim 4 wherein the cyclotron target is a bismuth target.

7. The method of claim 1 wherein the separation media is a non-PEG media.

8. The method of claim 1 wherein the separation media is a macroporous polymer resin.

\* \* \* \* \*